(12) United States Patent
Nishigishi

(10) Patent No.: US 9,446,217 B2
(45) Date of Patent: Sep. 20, 2016

(54) CATHETER

(71) Applicant: ASAHI INTECC CO., LTD., Nagoya-shi, Aichi (JP)

(72) Inventor: Makoto Nishigishi, Owariasahi (JP)

(73) Assignee: ASAHI INTECC CO., LTD., Nagoya (JP)

( * ) Notice: Subject to any disclaimer, the term of this patent is extended or adjusted under 35 U.S.C. 154(b) by 45 days.

(21) Appl. No.: 14/597,693

(22) Filed: Jan. 15, 2015

(65) Prior Publication Data
US 2015/0238727 A1    Aug. 27, 2015

(30) Foreign Application Priority Data
Feb. 24, 2014 (JP) ................. 2014-033196

(51) Int. Cl.
| | | |
|---|---|---|
| A61M 31/00 | (2006.01) | |
| A61M 37/00 | (2006.01) | |
| A61M 25/00 | (2006.01) | |
| A61M 25/01 | (2006.01) | |
| A61M 25/10 | (2013.01) | |

(52) U.S. Cl.
CPC ..... *A61M 25/0052* (2013.01); *A61M 25/0026* (2013.01); *A61M 25/0029* (2013.01); *A61M 25/0102* (2013.01); *A61M 25/10* (2013.01); *A61M 2025/0059* (2013.01)

(58) Field of Classification Search
CPC ........... A61M 25/10; A61M 25/0029; A61M 2025/0059; A61M 25/0052; A61M 25/0026; A61M 25/0102
USPC .................................. 604/103.09
See application file for complete search history.

(56) References Cited

U.S. PATENT DOCUMENTS

| | | | |
|---|---|---|---|
| 5,545,134 A | 8/1996 | Hilaire et al. | |
| 2003/0208221 A1 | 11/2003 | El-Nounou | |
| 2004/0019324 A1 | 1/2004 | Duchamp | |
| 2012/0296367 A1* | 11/2012 | Grovender | A61M 25/0012 606/192 |

FOREIGN PATENT DOCUMENTS

| | | |
|---|---|---|
| EP | 2 495 006 A1 | 9/2012 |
| JP | A-2003-164528 | 6/2003 |
| WO | WO 2006/126642 A1 | 11/2006 |

OTHER PUBLICATIONS

Jul. 21, 2015 Extended European Search Report issued in European Application No. 15154084.6.

\* cited by examiner

*Primary Examiner* — Jason Flick
(74) *Attorney, Agent, or Firm* — Oliff PLC

(57) ABSTRACT

A catheter that can efficiently transmit a pressing force applied to the distal end of the catheter without breaking at a midpoint of the catheter. The catheter includes a metal tube having a first wall and a second wall disposed in an outer tube, and a reinforcing member that is joined at its proximal end to an outer peripheral surface of the first wall. A distal end of the first wall extends distally beyond a distal end of the second wall and is bent toward the second wall. Thus, the second wall is not provided at a connected portion between the first wall and the proximal end of the reinforcing member, and the reinforcing member having a diameter increased at least by an amount corresponding to a thickness of the second wall can be disposed in the catheter without increasing the diameter of the outer tube.

5 Claims, 6 Drawing Sheets

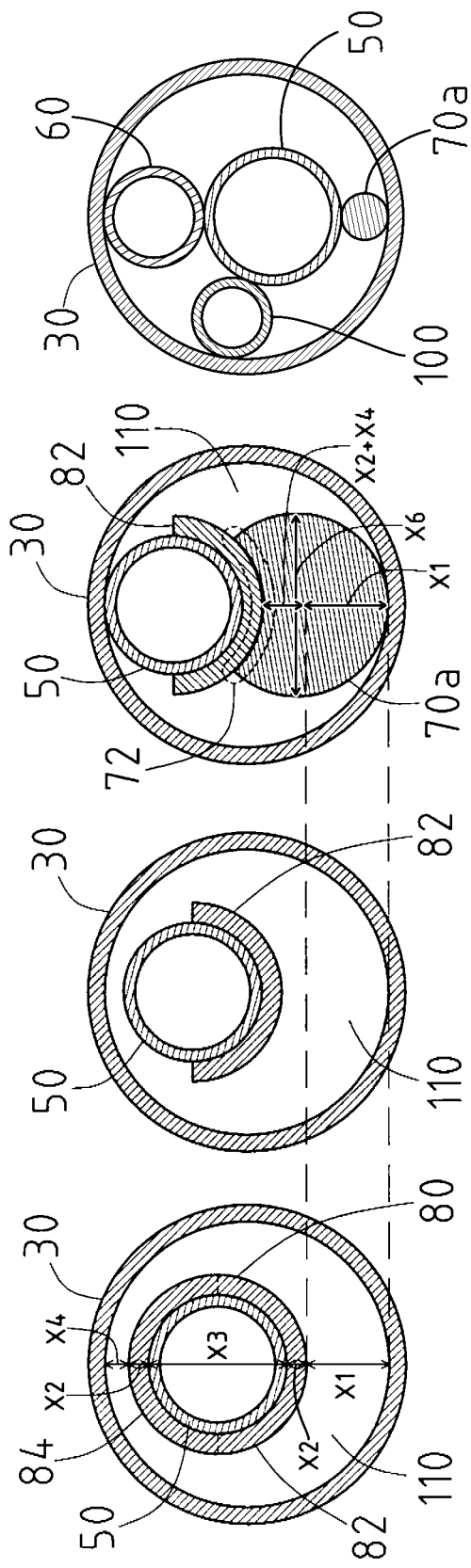

CATHETER

CROSS-REFERENCE TO RELATED APPLICATION

This application claims priority to Japanese Application No. 2014-033196 filed on Feb. 24, 2014, the contents of which are incorporated by reference herein in their entirety.

BACKGROUND

The disclosed embodiments relate to a medical device. Specifically, the disclosed embodiments relate to a catheter that can efficiently transmit a pressing force of an operator to the distal end of the catheter without being bent when being pressed by the operator in the distal direction of the catheter.

Conventionally, catheters are widely used for treating stenoses in blood vessels or alimentary canals. In order to press a catheter to a stenosis, a pressing force applied in the distal direction of the catheter needs to be efficiently transmitted to the end of the catheter.

As a method for such transmission, WO 2006/126642 discloses a catheter having a reinforcing member (core wire) in the longitudinal direction between an outer tube and an inner tube. In the catheter of WO 2006/126642, however, only the reinforcing member is inserted in the longitudinal direction. Unfortunately, this leads to insufficient stiffness, and thus a pressing force applied by an operator in the distal direction is hardly transmitted to the distal end of the catheter.

Japanese Patent Laid-Open No. 2003-164528 discloses a catheter with a metal tube having high stiffness at the proximal end operated by an operator, and a reinforcing member joined to the end of the metal tube. Since the stiff metal tube is provided at the proximal end, a pressing force applied by the operator in the distal direction can be transmitted from the metal tube to the distal end of the catheter through the reinforcing member.

In the catheter of Japanese Patent Laid-Open No. 2003-164528, however, the proximal end of the reinforcing member is joined to the inner peripheral surface of the metal tube, and thus another medical device inserted into the metal tube may be caught at the proximal end of the reinforcing member.

If the proximal end of the reinforcing member is directly joined to the outer peripheral surface of the metal tube to facilitate the insertion of another medical device into the metal tube, the metal tube improves the stiffness of the proximal end and increases the diameter of the outer tube. Unfortunately, this would increase the diameter of the overall catheter so as to prevent the catheter from reaching a site with stenosis on the end of a blood vessel or an alimentary canal. In order not to increase the diameter of the outer tube, the reinforcing member to be inserted into the outer tube needs to be reduced in diameter. Unfortunately, a reduction in the diameter of the reinforcing member would cause insufficient stiffness in the longitudinal direction of the catheter, causing a break on the catheter pressed by an operator in the distal direction.

SUMMARY

The disclosed embodiments have been devised in view of the above-discussed circumstances. An object of the disclosed embodiments is to provide a catheter in which a metal tube has a first wall and a second wall opposed to the first wall, and a distal end of the first wall extends distally beyond a distal end of the second wall and is bent toward the second wall, thereby allowing the diameter of the reinforcing member to be increased by an amount corresponding to the thickness of the second wall of the metal tube without increasing the diameter of the outer tube. A pressing force applied by the operator can therefore be efficiently transmitted to the distal end of the catheter without breaking the catheter.

The object is attained by the following solutions:

A catheter of the disclosed embodiments includes an outer tube, a metal tube inserted into the outer tube, an inner tube inserted into the metal tube, and a metallic reinforcing member extended in a longitudinal direction between the outer tube and the inner tube, wherein the metal tube has a first wall and a second wall opposed to the first wall, a distal end of the first wall extends distally beyond a distal end of the second wall and is bent toward the second wall, and the reinforcing member has a proximal end that is joined to the outer peripheral surface of the bent first wall.

In the catheter according to the disclosed embodiments, the proximal end of the reinforcing member may have a recess, so that the distal end of the first wall is joined to the reinforcing member at the recess.

Additionally, the catheter may further include a balloon attached to the front end of the inner tube, and a liquid supply tube provided along the inner tube so as to supply a liquid into the balloon, wherein the liquid supply tube has a proximal end that is connected to a lumen formed between the outer tube and the inner tube.

In the catheter according to the disclosed embodiments, a metal tube has a first wall and a second wall opposed to the first wall, a distal end of the first wall extends distally beyond a distal end of the second wall and is bent toward the second wall, and a proximal end of a reinforcing member is joined to an outer peripheral surface of the bent first wall. The second wall of the metal tube is not provided at a connected portion between the first wall of the metal tube and the proximal end of the reinforcing member. Thus, the reinforcing member having a diameter increased by an amount corresponding to the thickness of the second wall of the metal tube can be disposed in the catheter without increasing the diameter of the outer tube. Hence, when the operator presses the catheter in the distal direction, the catheter has sufficient stiffness in the longitudinal direction so as to reduce the occurrence of breaks in the catheter. This can efficiently transmit a pressing force, which is applied by the operator in the distal direction, to the distal end of the catheter.

When the proximal end of the reinforcing member has a recess, the distal end of the first wall of the metal tube is joined to the recess on the proximal end of the reinforcing member. Thus, the connected portion between the proximal end of the reinforcing member and the first wall of the metal tube may be the distal end of the first wall as well as the outer peripheral surface of the first wall. This can improve bonding strength between the reinforcing member and the metal tube. The provision of the recess on the proximal end of the reinforcing member can further increase the diameter of the reinforcing member in contact with the first wall of the metal tube. This can efficiently transmit a pressing force, which is applied by the operator in the distal direction, to the distal end of the catheter.

The catheter may further include a balloon attached to the distal end of the inner tube, and a liquid supply tube provided along the inner tube so as to supply a liquid into the balloon, wherein the liquid supply tube has a proximal end that is connected to a lumen formed between the outer tube and the inner tube. Thus, a liquid can be supplied into the balloon through the lumen formed between the outer tube and the inner tube and the liquid supply tube, inflating the balloon so as to fix the distal end of the catheter. This also fixes the distal end of the inner tube and improves the operability of another medical device inserted into the inner tube.

When the catheter includes the balloon, the liquid supply tube for supplying a liquid into the balloon is provided on the distal end of the catheter. When the catheter is inserted into a greatly curved blood vessel or alimentary canal, the distal end of the inner tube is considerably curved. Thus, the operator may unintentionally break the distal end of the inner tube when inserting another medical device into the inner tube. Even in this case, a liquid can be supplied into the balloon through the special liquid supply tube.

BRIEF DESCRIPTION OF THE DRAWINGS

FIG. 6A is a cross-sectional view taken along line A-A of FIG. 5, FIG. 6B is a cross-sectional view taken along line B-B of FIG. 5, FIG. 6C is a cross-sectional view taken along line C-C of FIG. 5, and FIG. 6D is a cross-sectional view taken along line D-D of FIG. 5.

DETAILED DESCRIPTION OF EMBODIMENTS

Figure 1:
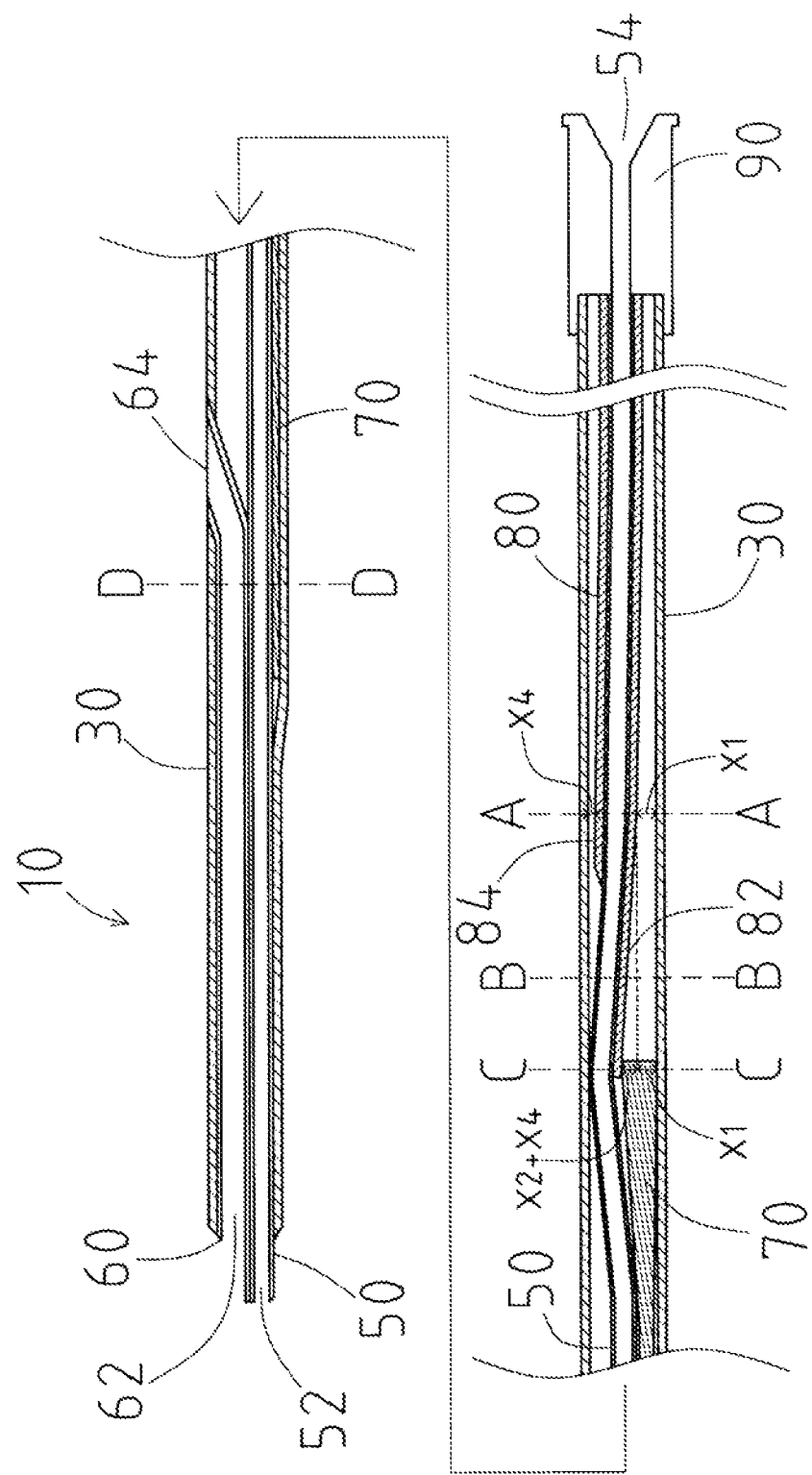
FIG. 1 is an overall view of a catheter according to the disclosed embodiments.
Figure 2:
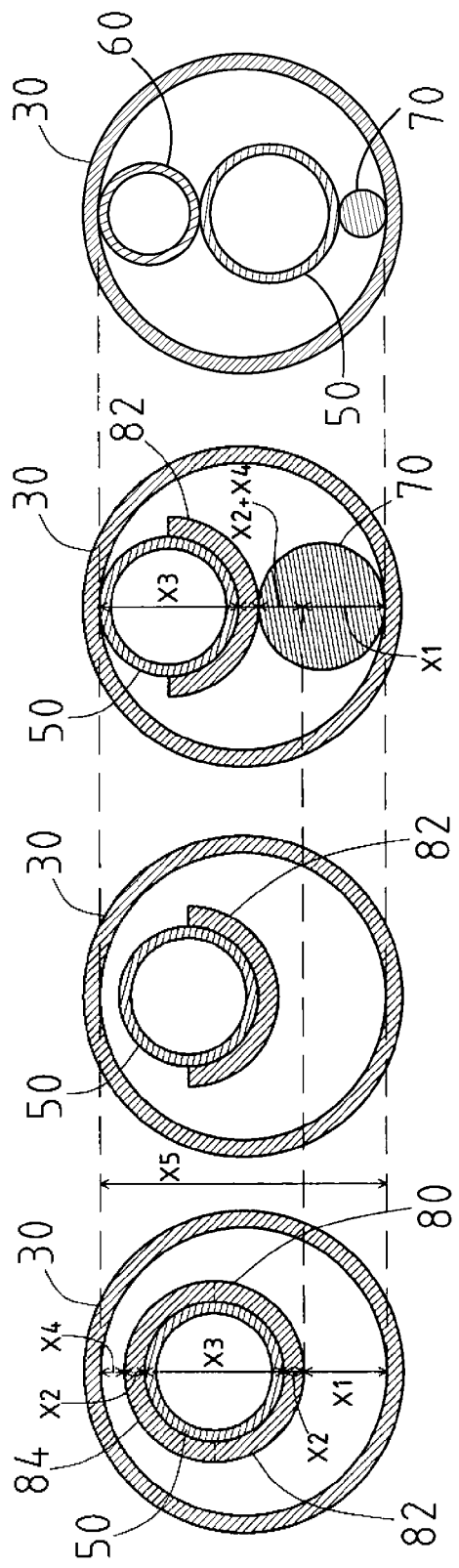
FIG. 2A is a cross-sectional view taken along line A-A of FIG. 1.
FIG. 2B is a cross-sectional view taken along line B-B of FIG. 1.
FIG. 2C is a cross-sectional view taken along line C-C of FIG. 1.
FIG. 2D is a cross-sectional view taken along line D-D of FIG. 1.

Referring to FIGS. 1 to 2D, a catheter 10 according to the disclosed embodiments will be described in the following example. In FIG. 1, the left side indicates a distal end to be inserted into a body while the right side indicates a proximal end to be operated by an operator, e.g., a doctor.

For example, the catheter 10 may be used for treating a stenosis formed in a blood vessel or an alimentary canal. As shown in FIG. 1, the catheter 10 mainly includes an outer tube 30, a first inner tube 50, a second inner tube 60, a reinforcing member 70, a metal tube 80, and a connector 90.

In the outer tube 30, the first inner tube 50 is inserted along the length of the catheter 10. Another medical device, e.g., a guide wire or a microcatheter, can be inserted into the first inner tube 50. In order to facilitate the insertion of another medical device, a connector 90 is connected to the proximal end of the outer tube 30 and the proximal end of the first inner tube 50. The distal end of the first inner tube 50 has a first distal-end opening 52 while a first insertion opening 54 is provided at the proximal end of the first inner tube 50 via the connector 90.

In the outer tube 30, the second inner tube 60 is inserted from a midpoint to the distal end of the catheter 10 in parallel with the first inner tube 50. As in the first inner tube 50, another medical device, e.g., a guide wire or a microcatheter, can be inserted into the second inner tube 60. The distal end of the second inner tube 60 has a second distal-end opening 62 while the proximal end of the second inner tube 60 has a second insertion opening 64.

Since the first inner tube 50 extends along the length of the catheter 10, the length of the first inner tube 50 may disadvantageously lead to difficulty in replacement of another medical device to be inserted by an operator. However, the insertion of another medical device into the first inner tube 50 may improve the stiffness of the catheter 10, advantageously allowing an operator to easily press the catheter 10 in the distal direction. Moreover, the second inner tube 60 only extends from a midpoint to the distal end of the catheter 10 and thus has a short length, advantageously allowing the operator to easily change another medical device inserted into the second inner tube 60. However, if another medical device is inserted only into the second inner tube 60, only the distal end of the catheter 10 increases in stiffness, disadvantageously causing the catheter 10 to break around the second insertion opening 64 of the second inner tube 60 that rapidly fluctuates in stiffness when the operator presses the catheter 10 in the distal direction. Since the catheter 10 includes the first inner tube 50 and the second inner tube 60, the operator can quickly change another medical device inserted into the second inner tube 60 while another medical device is inserted into the first inner tube 50. Furthermore, the catheter 10 is easily pressed in the distal direction.

A metal tube 80, a so-called hypotube, is inserted into the proximal end of the outer tube 30. The metal tube 80 is made of stainless steel or superelastic alloys such as a Ni—Ti alloy, providing stiffness to the proximal end of the catheter 10. The proximal end of the metal tube 80 is connected to the connector 90. The metal tube 80 has a lower first wall 82 and an upper second wall 84 opposed to the first wall 82. A distal end of the first wall 82 extends distally beyond a distal end of the second wall 84. The distal end of the first wall 82 is bent toward the second wall 84. The first inner tube 50 is inserted into the metal tube 80.

FIG. 2A is a cross-sectional view taken along line A-A of FIG. 1. FIG. 2B is a cross-sectional view taken along line B-B of FIG. 1. FIG. 2C is a cross-sectional view taken along line C-C of FIG. 1. In FIG. 2A, the metal tube 80 has a circular shape composed of the first wall 82 and the second wall 84. In FIGS. 2B and 2C, the metal tube 80 has a semicircular shape only composed of the first wall 82 because the second wall 84 is cut off from the distal end of the metal tube 80.

The catheter 10 further includes the metallic reinforcing member 70 that is longitudinally extended between the outer tube 30 and the first inner tube 50 (see FIG. 1). The reinforcing member 70 is a tapered metallic wire rod that is circular in cross section and decreases in diameter toward the distal end. The material of the reinforcing member 70 is not particularly limited. For example, stainless steel or superelastic alloys such as a Ni—Ti alloy can be used.

The reinforcing member 70 extends longitudinally along the first inner tube 50. The distal end of the reinforcing member 70 extends beyond the second insertion opening 64 of the second inner tube 60 toward the distal end of the catheter 10 (See FIGS. 1 and 2D). The proximal end of the reinforcing member 70 is joined to the outer peripheral surface of the first wall 82 that is bent toward the second wall 84 (See FIGS. 1 and 2C).

In FIG. 2A, X1 is a lower clearance between the outer peripheral surface of the metal tube 80 (first wall 82) and the inner peripheral surface of the outer tube 30, X2 is the thickness of the metal tube 80 (in other words, the thickness of each of the first wall 82 and the thickness of the second wall 84), X3 is the outside diameter of the first inner tube 50, X4 is an upper clearance between the outer peripheral surface of the metal tube 80 (second wall 84) and the inner peripheral surface of the outer tube 30, and X5 is the inside diameter of the outer tube 30. The relationship of X5=X1+X2+X3+X2+X4 is thus established. The total of the clearances between the outer peripheral surface of the metal tube 80 and the inner peripheral surface of the outer tube 30 is expressed as X1 (the clearance below the first wall 82)+X4 (the clearance above the second wall 84). Thus, a maximum diameter of a reinforcing member when joined at the proximal end to the outer peripheral surface of the metal tube 80, would typically be X1+X4.

However, in the catheter 10 of the disclosed embodiments, the second wall 84 is cut off and the first wall 82 is bent toward the second wall 84 (see FIG. 2C). Thus, although the inside diameter X5 of the outer tube 30 is kept constant in the longitudinal direction (in other words, without increasing the diameter of the outer tube 30), the diameter of the reinforcing member 70 is X5−X3 (the outside diameter of the first inner tube 50)−X2 (the thickness of the first wall 82)=X1+X2+X4. Thus, the reinforcing member 70 having a diameter increased by an amount corresponding to the thickness X2 of the second wall 84 of the metal tube 80 can be disposed in the catheter 10 without increasing the diameter of the outer tube 30. Hence, when an operator presses the catheter 10 in the distal direction, the catheter 10 has sufficient stiffness in the longitudinal direction so as to reduce the occurrence of breaks in the catheter 10. A pressing force, which is applied by the operator in the distal direction, can be efficiently transmitted to the distal end of the catheter 10.

In FIGS. 1 and 2B, the second wall 84 is completely cut off. However, the disclosed embodiments are not limited to this configuration. For example, the second wall 84 having the thickness X2 in the cross-sectional view taken along line A-A of FIG. 1 may be gradually reduced in thickness toward the distal end such that the thickness of the second wall 84 is smaller than X2 in the cross-sectional view taken along line B-B of FIG. 1 and the second wall 84 is not provided in the cross-sectional view taken along line C-C of FIG. 1. This configuration can gradually change the stiffness of the metal tube 80 toward the proximal end of the reinforcing member 70.

Figure 3:
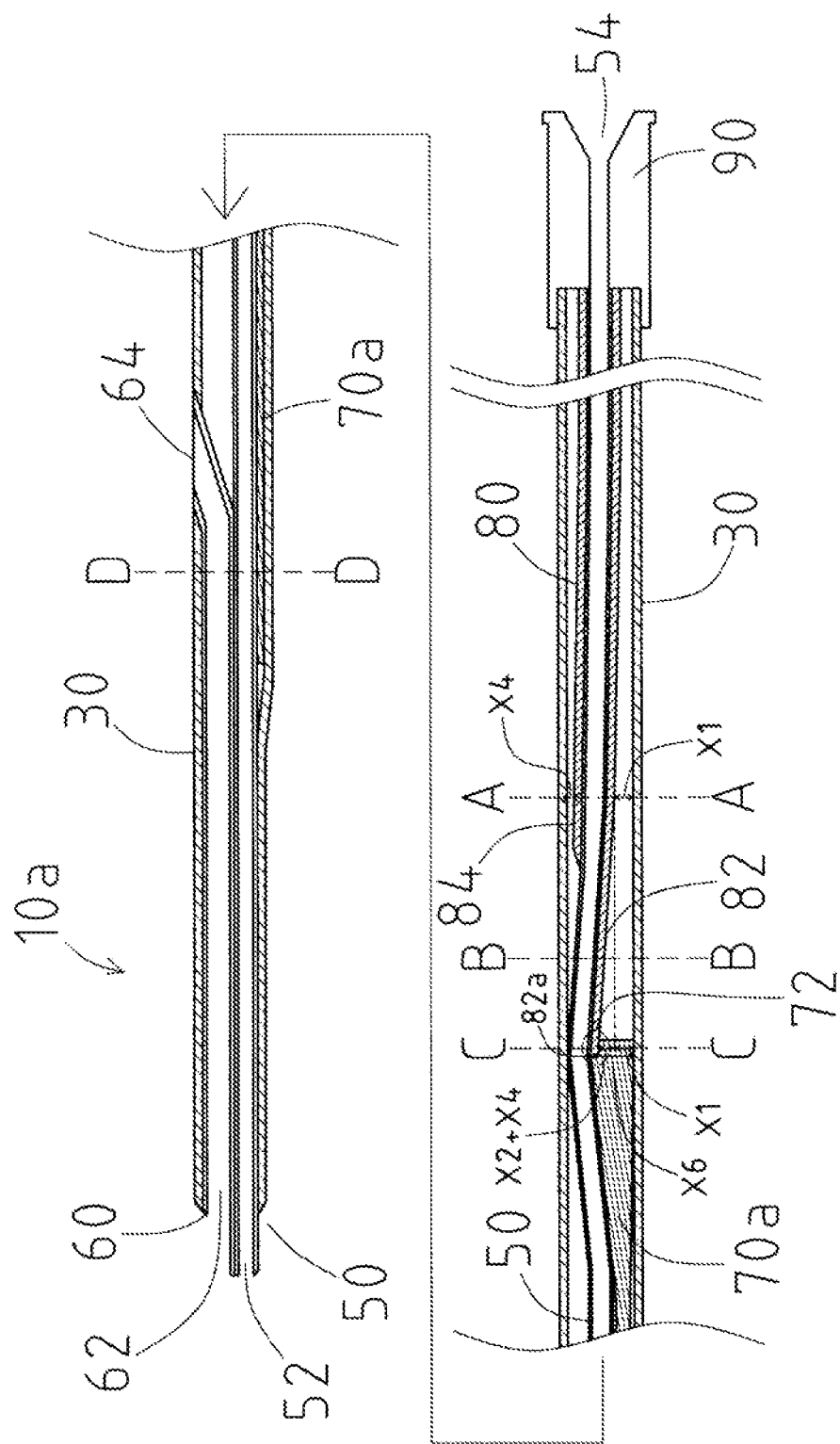
FIG. 3 is an overall view of a catheter where the proximal end of the reinforcing member has a recess, a modification of FIG. 1.
Figure 4:
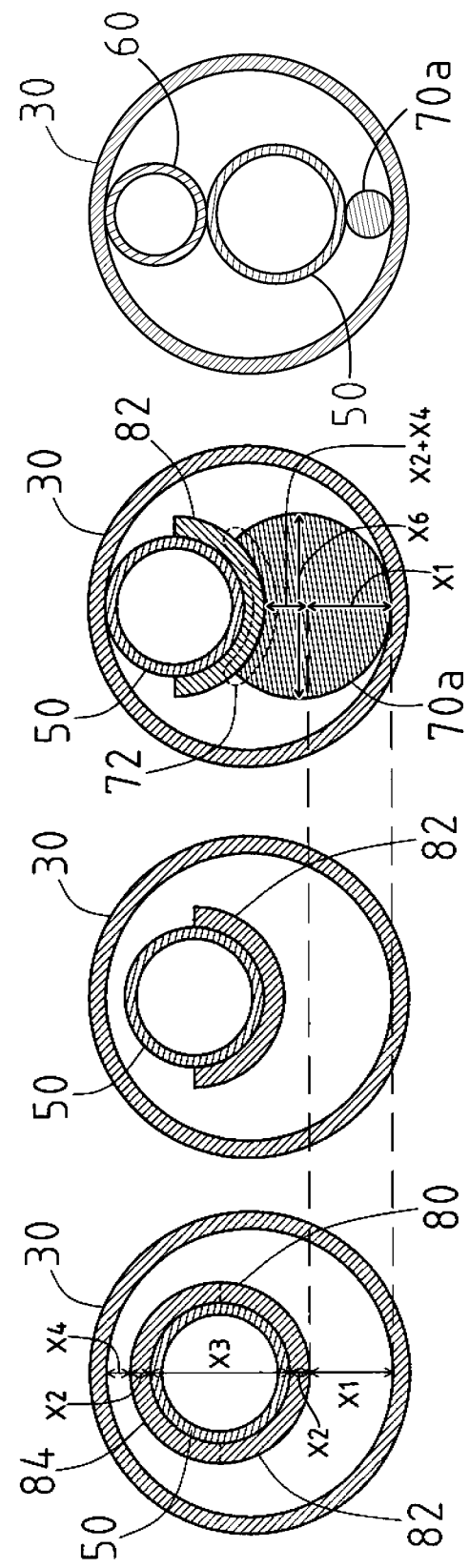
FIG. 4A is a cross-sectional view taken along line A-A of FIG. 3.
FIG. 4B is a cross-sectional view taken along line B-B of FIG. 3.
FIG. 4C is a cross-sectional view taken along line C-C of FIG. 3.
FIG. 4D is a cross-sectional view taken along line D-D of FIG. 3.

Referring to FIGS. 3 to 4D, a catheter 10a will be described below wherein the proximal end of the reinforcing member has a recess. In FIG. 3, as in FIG. 1, the left side indicates a distal end to be inserted into a body while the right side indicates a proximal end to be operated by an operator, e.g., a doctor.

Only the differences between the catheter 10 of FIGS. 1 to 2D and the catheter 10a of FIGS. 3 to 4D will be described below. In the catheter 10a, a recess 72 is formed on the proximal end of a reinforcing member 70a while the distal end of a first wall 82 of a metal tube 80 is joined to the recess 72 of the reinforcing member 70a (see FIGS. 3 and 4C). Like the reinforcing member 70, the reinforcing member 70a is a tapered metallic wire rod that is circular in cross section and is reduced in diameter toward the distal end. The reinforcing member 70a has a diameter X6 that is maximized at a contact point with a front end 82a of the first wall 82 of the metal tube 80. The diameter X6 is larger than the diameter X1+X2+X4 of the reinforcing member 70 (X6>X1+X2+X4). The recess 72 of the reinforcing member 70a is formed so as to fit to the front end 82a of the first wall 82. The reinforcing member 70a on the recess 72 has a diameter of X1+X2+X4 like the reinforcing member 70 (See FIG. 4C).

With this configuration, the catheter 10a has the recess 72 on the proximal end of the reinforcing member 70a, further increasing the surface area of the reinforcing member 70a that is in contact with the front end 82a of the first wall 82 of the metal tube 80. Moreover, the proximal end of the reinforcing member 70a and the first wall 82 of the metal tube 80 are joined to each other on the front end 82a of the first wall 82 as well as the outer peripheral surface of the first wall 82. This can increase bonding strength between the reinforcing member 70a and the metal tube 80. Hence, a pressing force applied by the operator in the distal direction can be more efficiently transmitted to the distal end of the catheter 10.

Figure 5:
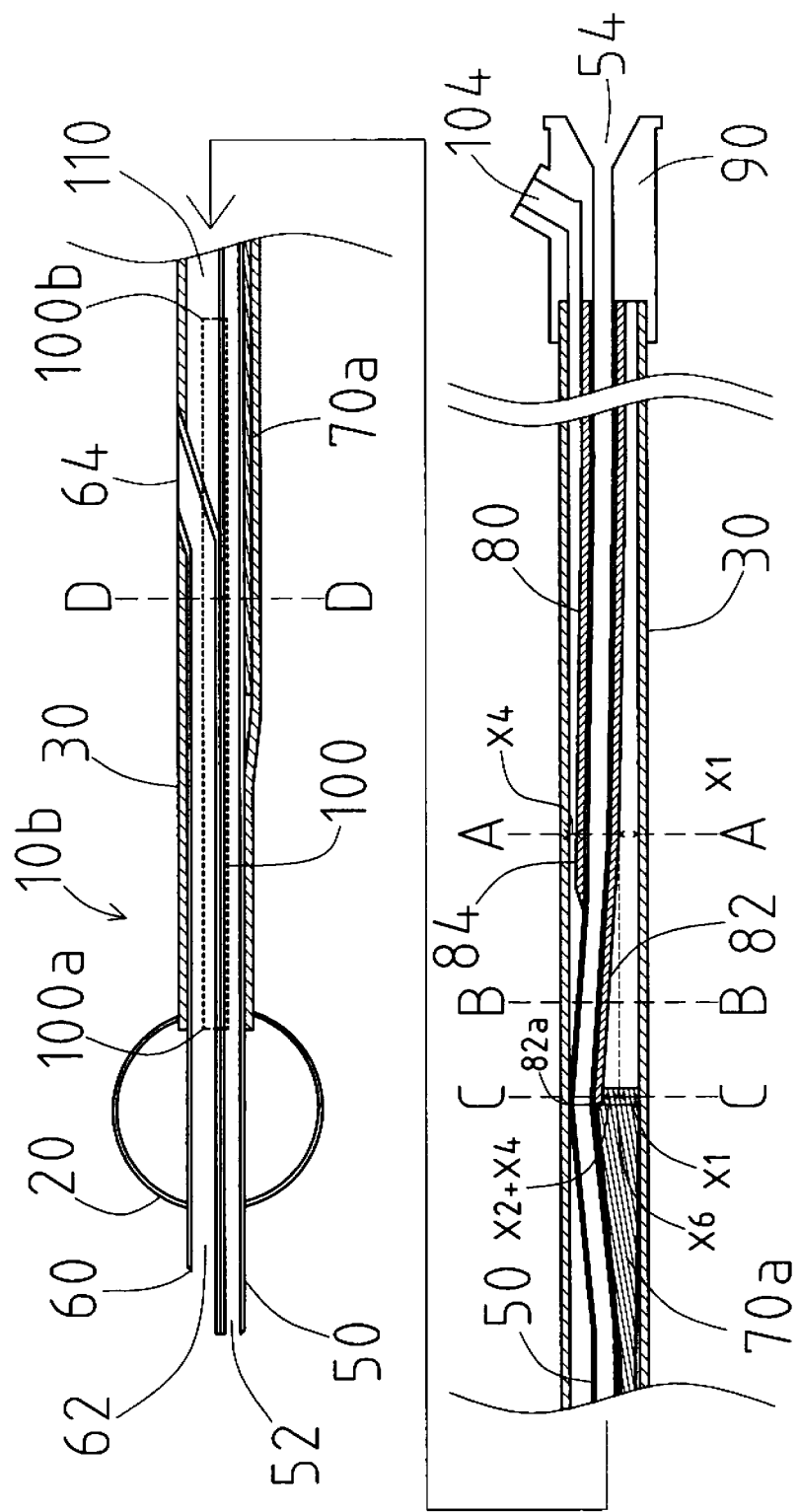
FIG. 5 is an overall view of a catheter having a balloon.

Referring to FIGS. 5 to 6D, a catheter 10b having a balloon will be described below. As in FIGS. 1 and 3, in FIG. 5, the left side indicates a distal end to be inserted into a body while the right side indicates a proximal end operated by an operator, e.g., a doctor.

Only the differences between the catheter 10a in FIGS. 3 to 4D and the catheter 10b of FIGS. 5 to 6D will be described below. In the catheter 10b, a balloon 20 is attached to the front end of an outer tube 30 and the front end of a first inner tube 50. The outer tube 30 has a liquid supply tube 100 for supplying a liquid, such as a contrast medium and a physiological saline, for inflating the balloon 20, the liquid supply tube 100 being provided along the first inner tube 50 and the second inner tube 60. The liquid supply tube 100 has a distal end 100a that extends into the balloon 20. The liquid supply tube 100 has a proximal end 100b that extends beyond a second insertion opening 64 of the second inner tube 60 toward the proximal end of the catheter 10b and communicates with a lumen 110 formed between the outer tube 30 and the first inner tube 50 (see FIG. 5).

As shown in FIG. 5, when a liquid for inflating the balloon 20 is supplied from an indeflator (not shown) attached to a liquid inlet port 104 of a connector 90, the liquid is supplied to the balloon 20 through the lumen 110 (see FIGS. 6A to 6D) on the proximal end of the catheter 10b and through the liquid supply tube 100 (see FIG. 6D) from a midpoint to the distal end of the catheter 10b. The balloon 20 when inflated against a blood vessel wall or an alimentary canal wall fixes the distal end of the catheter 10b, thereby fixing the distal end of the first inner tube 50. This can improve the operability of another medical device inserted into the first inner tube 50.

If a stenosis is located on the end of a blood vessel or an alimentary canal, the distal end of the catheter 10b inserted into the blood vessel or the alimentary canal is greatly curved. Thus, the distal end of the first inner tube 50 inserted into the outer tube 30 is also greatly curved. In this state, if an operator inserts another medical device into the first inner tube 50, the medical device may break the greatly curved first inner tube 50.

In the catheter 10b, the liquid supply tube 100 is positioned from a midpoint to the distal end of the catheter 10b. Thus, even if an operator unintentionally breaks the first inner tube 50 with the greatly curved distal end when inserting another medical device into the first inner tube 50, a liquid can still be supplied to the balloon 20. The liquid supply tube 100 is not provided along the entire length of the catheter 10b. The proximal end 100b of the liquid supply tube 100 is connected to the lumen 110 instead. The lumen 110 is larger in cross-sectional area than the liquid supply tube 100 (see FIGS. 6A to 6D). Thus, a liquid passage extends from the proximal end where another medical device is unlikely to break the tube. This configuration can shorten a time period for supplying a liquid into the balloon 20 or a time period for collecting the liquid from the balloon 20, achieving a smooth operation.

In FIGS. 1 to 6D, the catheters 10, 10a, and 10b each have the second inner tube 60. In the disclosed embodiments, however, the second inner tube 60 is not always necessary and thus may be optionally omitted.

In the catheters 10, 10a, and 10b, the second wall 84 of the metal tube 80 is not provided, the first wall 82 is bent toward the second wall 84, and the proximal ends of the reinforcing members 70 and 70a are each joined to the outer peripheral surface of the bent first wall 82. Thus, the reinforcing members 70 and 70a having a diameter increased at least by an amount corresponding to the thickness X2 of the second wall 84 can be disposed in the catheter 10 without increasing the diameter of the outer tube 30. Hence, when an operator presses the catheter 10 in the distal direction, the catheter 10 has sufficient stiffness in the longitudinal direction so as to reduce the occurrence of breaks in the catheter 10. A pressing force, which is applied by the operator in the distal direction, can thus be efficiently transmitted to the distal end of the catheter 10.

What is claimed is:

1. A catheter comprising:
   an outer tube;
   a metal tube inserted into the outer tube;
   a first inner tube inserted into the metal tube; and
   a reinforcing member inserted between the outer tube and the first inner tube and extending in a longitudinal direction,
   wherein:
      the metal tube has a first wall and a second wall opposed to the first wall, and a distal most end of the first wall extends distally beyond a distal most end of the second wall and is bent toward the second wall, and
      a proximal most end of the reinforcing member has a recess, and the distal most end of the first wall does not extend distally beyond the recess.

2. The catheter according to claim 1, wherein the reinforcing member is metallic.

3. The catheter according to claim 1, further comprising:
   a second inner tube extending within the outer tube from a point between distal and proximal ends of the catheter to the distal end of the catheter.

4. The catheter according to claim 1, further comprising:
   a balloon attached to a distal end of the first inner tube; and
   a liquid supply tube inserted into the outer tube and provided along the first inner tube so as to supply a liquid into the balloon,
   wherein:
      the liquid supply tube has a proximal end that is connected to a lumen formed between the outer tube and the first inner tube.

5. A catheter comprising:
   an outer tube;
   a metal tube inserted into the outer tube;
   a first inner tube inserted into the metal tube; and
   a reinforcing member inserted between the outer tube and the first inner tube and extending in a longitudinal direction,
   wherein:
      the metal tube has a first wall and a second wall opposed to the first wall, and a distal most end of the first wall extends distally beyond a distal most end of the second wall and is bent toward the second wall,
      the reinforcing member has a proximal most end that is joined to an outer peripheral surface of the bent first wall, and
      a diameter of the proximal most end of the reinforcing member is equal to a sum of (i) a total distance between an outer peripheral surface of the first wall and an inner peripheral surface of the outer tube, (ii) a total thickness of the second wall, and (iii) a total distance between an outer peripheral surface of the second wall and the inner peripheral surface of the outer tube.

* * * * *